US005733576A

United States Patent [19]

Chmelir

[11] Patent Number: 5,733,576
[45] Date of Patent: Mar. 31, 1998

[54] PROCESS FOR THE PRODUCTION OF ABSORBING MATERIAL WITH AN IMPROVED DEGRADABILITY AND ABSORPTION FOR WATER, AQUEOUS SOLUTIONS AND BODY LIQUIDS, AND ITS USE IN HYGIENIC ARTICLES AND FOR SOIL CONDITIONING

[75] Inventor: Miroslav Chmelir, Krefeld, Germany

[73] Assignee: Chemische Fabrik Stockhausen GmbH, Krefeld, Germany

[21] Appl. No.: 343,280

[22] Filed: Nov. 21, 1994

Related U.S. Application Data

[63] Continuation of Ser. No. 57,194, May 3, 1993, abandoned, which is a continuation of Ser. No. 761,072, Sep. 17, 1991, abandoned.

[30] Foreign Application Priority Data

Sep. 19, 1990 [DE] Germany ............... 40 29 593.1

[51] Int. Cl.$^6$ ...................................... A61K 9/14
[52] U.S. Cl. .................. 424/488; 424/484; 424/489; 424/486
[58] Field of Search ................ 424/488, 484, 424/489, 486

[56] References Cited

U.S. PATENT DOCUMENTS

| | | | |
|---|---|---|---|
| 4,429,001 | 1/1984 | Kolpin et al. | 428/283 |
| 4,500,670 | 2/1985 | McKinley et al. | 524/445 |
| 4,605,401 | 8/1986 | Chmelir et al. | 604/368 |
| 4,892,754 | 1/1990 | Itoh et al. | 427/54.1 |
| 5,006,339 | 4/1991 | Bargevy et al. | 424/404 |
| 5,013,769 | 5/1991 | Murray et al. | 523/111 |
| 5,041,292 | 8/1991 | Feijen | 424/484 |

FOREIGN PATENT DOCUMENTS

| | | | |
|---|---|---|---|
| 1570485 | 7/1980 | United Kingdom | C08J 9/42 |

*Primary Examiner*—Thurman K. Page
*Assistant Examiner*—Kathryne E. Shelborne
*Attorney, Agent, or Firm*—Sprung Kramer Schaefer & Briscoe

[57] ABSTRACT

A process for the production of absorbing agents for water, aqueous solutions and body liquids consisting of at least two components A and B, whereby component A comprises a water-swellable, synthetic polymer or copolymer and component B comprises a natural or synthetic polymeric compound which at normal temperature is a pourable powder and is partially soluble or insoluble in water. Component B is added to component A in dry or partially swollen form during component A's production process after a monomer conversion of at least 30%, preferably at least 60% is attained, and is then mixed with the polymer gel of component A and subsequently dried. The invention further relates to the use of the absorbing agent for the absorption and/or retention of water and/or aqueous solutions, in particular of aqueous body liquids, such as urine or blood, in absorbent expendable products for hygienic, surgical and other medical purposes, such as diapers, tampons, and sanitary napkins; for the absorption and/or retention of water and/or aqueous solutions and subsequent controlled release of water and/or the substances dissolved in the aqueous medium to other bodies, as well as for drying gases and/or liquids, preferably organic liquids and solvents which are not miscible in water.

13 Claims, No Drawings

PROCESS FOR THE PRODUCTION OF ABSORBING MATERIAL WITH AN IMPROVED DEGRADABILITY AND ABSORPTION FOR WATER, AQUEOUS SOLUTIONS AND BODY LIQUIDS, AND ITS USE IN HYGIENIC ARTICLES AND FOR SOIL CONDITIONING

This application is a continuation of application Ser. No. 08/057,194, filed May 3, 1993, now abandoned, which is a continuation of Ser. No. 07/761,072, filed Sep. 17, 1991, now abandoned.

The present invention relates to a process for the production of absorbers consisting of a combination of synthetic polymers and, preferably, natural polymers, such as polysaccharides, which absorbers rapidly absorb water and aqueous liquids, and are used, e.g., for absorptive expendable products in hygienic articles, such as diapers and sanitary towels, and for other medical purposes, or as water-storing soil conditioners.

Absorbents having a high absorption capacity for water and body liquids are known. Those belonging to the fully synthetic absorbing agents are cross-linked polymers and copolymers on the basis of acrylic or methacrylic acid (German OS [Offenlegungsschrift, publication of a German patent application] Nos. 24 29 236, 26 14 662, 27 12 043, 26 53 135, 26 50 377, 28 13 634; U.S. Pat. Nos. 4,018,951, 3,926,891, 4,066,583, 4,062,817), maleic acid derivatives (according to U.S. Pat. No. 4,041,228), or acrylamidopropane sulfonic acid copolymers (according to German Pat. No. 31 24 008). These known synthetic absorbers are practically water-insoluble, absorb the multiple amount of their weight of water, urine, or other aqueous solutions, however, are relatively resistant to biodegradability.

Other products were produced on a starch basis, e.g., starch acrylonitrile graft polymers (U.S. Pat. Nos. 3,997,484, 3,661,815, 4,155,888, 3,935,099), gelatinized starch derivatives (German OS 27 02 781), or on a cellulose basis, such as derivatives of alkyl- or hydroxyalkyl cellulose (JP-Pat. No. 77/125 481), carboxymethylcellulose (BE-Pat. No. 862 130 and GB-Pat. No. 1 59 949) and on a polysaccharide basis (German OS 26 50 377). Although these products, such as the starch polymers grafted with acrylonitrile or acrylic acid, belong to the decomposable products, their production is very expensive, and the amount of the natural product in the end product is very limited due to the high viscosity of the reaction medium, e.g., in case of a monomer solution with dissolved starch. The monomer solution according to European Pat. No. 0 372 981, Example 11, for instance, only contains approximately 4%-wt. of dissolved starch, relative to the total batch.

According to German Pat. No. 21 43 549, starch products, dextrin, or flour are used to powder the gelatinous granular material of polyacrylamide polymers to obtain storable, non-agglomerating, dimensionally stable gelatinous granular material with a high content of water. Said material is proposed for the use as water-soluble flocculation and sedimentation auxiliary agents.

In this case, the starch is distributed only on the surface of the hydrous polymer gel particles of the water-soluble product. On the first contact with water, the starch is substantially washed off the surface of the powdered polymer gel. There is no incorporation of the starch into the swollen polyacrylamide gel.

As a consequence, a procedure of directly adding the natural product (referred to as "component B" hereinafter) to the monomer solution of component A (synthetic polymer), homogenizing, and then starting the polymerization may be carried out only in case of low contents of 2 to a maximum of 5%-wt. of component B in the monomer solution. For technical and economic reasons, however, the monomer concentration of the monomer solution is between 20 to 30%-wt. Such processes are described, e.g., by German Pat. No. 26 12 846, British Pat. No. 1490128, and European Pat. No, 0 189 163, Efforts to dissolve quantities above 5%-wt. of component B in the monomer solution, result in highly viscous to gel-like monomer solutions which cannot be stirred and thus prevent homogeneous mixing with the catalyst solutions so that an even polymerization conducted to a high reaction degree is rendered impossible.

According to German OS 22 64 027, inert filling agents, such as wood flour, pulp fibers, cellulose or nylon floccules, slag, clay, fly ash, coal dust, and fertilizers, are used as additives during the crosslinkage of the water-soluble polymers. The uncrosslinked, water-soluble polymers or copolymers, respectively, are mixed as dry powder with the inert fillers; after the mixture has been sprayed with 15 to 85%-wt., or even more, water (in the major part of the examples 200 to 400%-wt. water, relative to the mixture of polymer and filler are used) the resultant water-containing granulate is cross-linked by ionizing radiation (0.05 to 20.0 MeV). After drying, a partially water-insoluble polymeric absorber results which absorbancy for water is approximately five- to forty-fold the amount of the dry weight.

It is the object of the present invention to provide a process enabling the incorporation of the known synthetic polymers with high absorption capacity for water and aqueous liquids, such as urine or blood, and used as absorbents by means of additives which on their own have a comparatively low absorption capacity for such liquids, without significantly deteriorating the absorption capacity of the end product, even if larger amounts of poorly absorbing additives are incorporated. Also the degradability is improved in certain cases.

This object is achieved according to the present invention by the characterizing features of claim 1.

The manufacture of component A is carried out according to known methods. It may be effected discontinuously as swollen polymer gel in a polymerization vessel, or continuously on a continuous belt, According to German Pat. No. 35 44 770, e.g., the polymerization is carried out in an aqueous solution containing the water-soluble monomer and, optionally, the comonomers at a concentration of 2.2 to 8.3 mols of polymerizable double bonds per kilogram of monomer solution, in particular 3.5 to 6.25 mols (corresponding to 16 to 60%-wt., particularly 25 to 45%-wt. acrylic acid, if it is used as monomer) and within a temperature range of approximately −10° to 120° C.

The polymers of acrylic acid and methacrylic acid alone as homopolymer or as copolymer are primarily suitable for the use as component A, but also the polymers of other water-soluble monomers, such as acrylamide, as well as polymerizable acids and the salts thereof, in particular maleic acid, fumaric acid, itaconic acid, vinyl sulfonic acid, or 2-acrylamido-2-methylpropane sulfonic acid. Further examples are hydroxyl-groups-containing esters of polymerizable acids, in particular the hydroxyethyl- and hydroxypropyl esters of acrylic and methacrylic acid; as well as amino-groups-containing and ammonium-groups-containing esters and amides of polymerizable acids, such as the dialkylamino esters, in particular the dimethyl- and the diethylaminoalkyl esters of acrylic and methacrylic acid, as well as the trimethyl- and triethylammonium alkylesters and the corresponding amides. In addition, small amounts of cross-linking monomers, e.g., monomers having more than one polymerizable group within the molecule, are polymerized together with the above-mentioned monomers.

The above-mentioned monomers may be polymerized alone to form cross-linked homopolymers, or with one another to form cross-linked copolymers.

In addition, small amounts of monomers which are slightly or even insoluble in water, such as (meth) acrylonitrile, vinyl pyridine, and vinyl acetate may be copolymerized, such as the esters of acrylic and/or methacrylic acid with $C_1$–$C_{10}$-alcohols, styrene and alkylated styrenes. In general, the proportion of water-soluble monomers is in the range of 40 to 100%-wt., relative to the total amount of monomers. The proportion of the cross-linking monomers is in the range of 0 to 20%-wt., preferably 0.01 to 2.0%-wt., relative to the total monomer amount. In general, the amount of water-insoluble, hydrophobic monomers is 0 to 40%-wt. of the monomers.

Examples of cross-linking monomers include bi- and polyfunctional monomers, e.g., amides, such as the methylene bisacryl- or -methacrylamide or ethylene bisacrylamide, in addition esters of the unsaturated mono- or polycarboxylic acids of polyols, such as diacrylates or triacrylates, e.g., butanediol- or ethylene glycol diacrylate or -methacrylate, trimethylolpropane triacrylate, as well as vinyl methacrylate and allyl compounds, such as allyl(meth) acrylate, triallyl cyanurate, maleic acid diallyl ester, polyallyl ester, tetraallyl oxiethane, triallylamine, tetraallyl ethylene diamine, allyl ester of the phosphoric acid or phosphorous acid, respectively, as well as cross-linkable monomers, such as the N-methylol compounds of amides, such as methacrylamide or acrylamide and the ethers derived therefrom.

The polymerization may be initiated by chemical catalysis and/or high-energy radiation/light. Suitable catalysts, for example, are peroxy compounds, such as potassium peroxydisulfate, hydrogen peroxide, organic peroxides, such as benzoyl peroxide, tert-butyl hydroperoxide, tert-butyl perpivalate; redox systems, such as potassium-peroxydisulfate-sodium-disulfite, hydrogen peroxide hydroxylamine chloride, or azoinitiators, such as AIBN [2,2'-azobis-(isobutyronitrile)] or 2,2'-azobis(2-amidinopropane)dihydrochloride. Examples of suitable photoinitiators include benzoin and the derivatives thereof, e.g., benzoin ether, such as benzoin-ethyl-propyl-ether, benzil and the derivatives thereof, such as benzil ketals or aryl diazonium salts, acetophenone derivatives, and others, alone or in admixtures. In general, the content of photoinitiators is in the range of 0.002 to 2.0%-wt., preferably 0.01 to 0.2%-wt., relative to the monomers used. The content of catalysts generally is in the range of 0.02 to 5.0%-wt., preferably between 0.20 to 2.0%-wt., relative to the monomers.

According to the present invention, natural polymers based on polysaccharide are used as component B, examples thereof include modified cellulose and cellulose derivatives, e.g., alkyl-, hydroxyalkyl-, carboxymethylcellulose, gum resins, e.g., guar gum, locust bean gum, tragacanth gum, gum arabic, pectin, etc.; starch and starch derivatives, such as corn starch, grain starch, potato starch, amylose, amylopectin, dextrin, dextran, modified starch, hydroxyethyl starch, cationic starch, starch graft polymers, etc.

In addition to said natural polymers used as component B, also other materials with a large surface may be used, e.g., fibrous material of natural fibers, preferably fibers of cotton, hemp, wool, and silk, furthermore fibrous material of cellulose fibers, such as viscose, acetate- and triacetate fibers, or of synthetic fibers based on polyester, polyolefins, polyacrylonitrile, polyamide, polyvinyl alcohol, polyvinyl acetate, and polyvinyl chloride, polyurethane, polyvinyl urea, as well as the copolymers of these polymers. The fibrous materials may preferably be incorporated into component A in the form of short fibers having a length of 0.1 to 60 mm.

Additional materials may also be used as additive, for example, odoriferous substances to perfume the final product, disinfectants, antibacterial agents, but also neutral fillers, such as wood flour, peat, ground shells of walnuts or pomaceous fruit, chitin-containing flour, sand, garden mold, or other extenders.

Finally, it is also possible to add as component B only the finely ground component A in dried powder or partially swollen form to the polymer gel of component A.

The process according to the present invention consists in the fact that component B is added to the swollen polymer gel of component A as a powder in dry or slightly moist or swollen form during the manufacture of the synthetic-polymer (component A). Advantageously, component B is added to the swollen polymer gel of component A only during the end phase of the production of component A, i.e., not before a reaction conversion of more than 30%, preferably more than 60%, and in particular preferred more than 95% is achieved, and it is then mixed with the polymer gel and subsequently dried.

Mixing the two components may be carried out in a suitable mixer. Advantageously, a mixer with rotary stirring mechanism is used. A suitable mixer, for example, consists of a vertically or horizontally positioned metal cylinder the stirrer of which is provided with guide blades thoroughly wiping the walls of the mixer drum.

A trough kneader with double-U-shaped cross-section may also be used to mix the two components A and B evenly. Within said trough, a pair of kneading shafts is moving in the same or opposite direction at the same or different speed; the form of the blades may also be selected in accordance with the material to be mixed. For continuous operation, the trough kneader may be provided with a discharging cylinder and a discharge screw which either works in reverse rotation to the interior of the trough thus intensifying the mixing and kneading process, or is switched in reversed direction of the material discharge.

Examples of other suitable devices for continuous operation include: single-shaft mixers, such as a single-screw extruder, ko-kneaders, two-shaft mixers with twin worm operating in the same or opposite direction, conical cotruder-screw, double-shaft continuous kneader, and continuous multi-shaft devices, e.g., a four-screw extruder.

After mixing, the mass of polymer gel is dried at a temperature within a range of 50° to 160° C. An end product is obtained in which the component B (e.g., a natural polymer) is incorporated in the synthetic polymer in such a way that the water-extractable portions of the end product—compared to a physical mixture of components A and B—are significantly smaller, preferably 30%-wt. and in particular below 20%-wt.

The incorporation of component B into the synthetic polymer may be intensified by adding different, above-mentioned catalysts in an amount of 0.01 to 2.0%-wt., and/or the above-mentioned polyfunctional monomers in an amount of 0.05 to 5.0%-wt. to component B or component A. The catalysts or polyfunctional compounds may be sprayed, for example as a solution, on component A or B either prior to or during mixing.

Low- or high-molecular, water-soluble or water-swellable polymers on a synthetic or natural basis (e.g., polysaccharides in dissolved or swollen condition) may additionally be used as auxiliary binding agents to support the linkage of the two components A and B. Examples of water-soluble or water-swellable polymers on a synthetic basis are polymers or copolymers based on (meth-)acrylic acid or (meth-)acrylic acid derivatives, such as the homo- or copolymers of acrylic acid, methacrylic acid, 2-acrylamido-2-methylpropane sulfonic acid, of the salts of these acids, of the acrylamide or methacrylamide, with one another or with vinyl pyrrolidone and/or vinyl acetate, as well as polyvinyl alcohol.

However, it is also possible to employ low- or high-molecular polymers being present as emulsion polymers in an aqueous dispersion in the form of tiny spherical particles solubilized by an emulsifier, whereby both forms of emulsion "oil-in-water" (for water-insoluble polymers) and "water-in-oil" (for water-soluble polymers) are possible. As is generally known, the oil phase in most cases consists of organic solvents which are not miscible with water, such as aliphatic or aromatic hydrocarbons (e.g., hexane, white oil).

Examples of polymers capable of forming oil-in-water emulsions include polymers of butadiene, styrene, isoprene, chloroprene, acrylonitrile, vinyl acetate, vinyl- and vinylidene chloride, alkylacrylates and alkylmethacrylates, and copolymers of these monomers with one another or with methyl styrene, isobutylene, or ethylene.

Examples of polymers which are used in water-in-oil emulsions include the above-mentioned water-soluble or water-swellable polymers or copolymers on the basis of (meth-)acrylic acid derivatives, which may be crosslinked or not.

The following examples demonstrate that the end products of component A and B produced according to the process of the present invention have an improved absorption capacity for synthetic model urine solution (examples 1 to 8) and they exhibit a considerably improved degradability (example 16).

The final product consists of the components A and B at a weight ratio of 20 to 98%-wt, preferably 40 to 95%-wt. of component A, and 2 to 80%-wt., preferably 5 to 60%-wt. of component B.

Test methods

1) In order to determine the rate of absorption, the absorp-tion of model urine is carried out according to the Demand-Absorbency-Test (DAT-method according to W. F. Schlauch, lecture index 1978, Amsterdam); the absorption rate after 60 seconds, as well as the maximum absorption and the retention are determined. The measuring instrument consists of a burette filled with the model urine solution (2.0% urea, 0.9% NaCl, 0.1% $MgSO_4$, and 0.06% $CaCl_2$, dissolved in distilled water) and a table provided with an outlet opening for the model urine solution connected to the measuring burette. On the table, which was covered with a thin non-woven (10×13.5 cm), 0.5 g of the product according to the present invention, mixed with 5 mg Aerosil 200 (Degussa AG), is evenly sprinkled on the middle of the liquid outlet in the form of a circular area having a diameter of 4.5 cm. The contact of the model urine solution with the powder product is effected by closing the hose and slight pressure loading; the solution of model urine may now be absorbed by the product according to the present invention. After 20 to 30 minutes, the absorbed amount of model urine solution is read as maximum value. Subsequently, the retention was determined by loading the swollen gel with a weight of 10 g/cm$^2$; loading is effected for 5 minutes. The determined retention values are tabulated in the examples.

2) A tea bag test was carried out as additional method to determine the rate of liquid absorption. The liquid absorp-tion of 0.2 g test substance without added Aerosil was gravimetrically determined in a tea bag after 10 minutes (maximum value) and after centrifuging, e.g., in a commercial spin dryer at 1400 rpm, this value was then converted to 1 g of product (retention value). The aqueous 0.9% NaCl-solution was used as test liquid.

3) Artificial decomposition conditions effected by irradiation similar to daylight were simulated with a Xenotest lamp and exposure times of 30, 60, and 90 minutes using a polymer gel swollen with water (200 g water per 1 g product). The swollen polymer gel was exposed to the Xenotest lamp, and after certain intervals of time, the degradability of the polymer gel was assessed according to a scale with 1 to 8 grades (Example 16).

Grade 1: gel structure unchanged

Grade 2: gel structure slightly changed

Grade 3: gel structure still detectable, but slight flow

Grade 4: gel structure extremely flown

Grade 5: gel structure not detectable, a highly viscous liquid

Grade 6: low viscous liquid

Grade 7: liquid ressembling water

Grade 8: water completely evaporated

The Xenotest lamp corresponds to natural daylight in the spectral region; the method was developed by Cassella Farbwerke, Mainkur AG, Frankfurt, FRG.

EXAMPLES 1 TO 3

330 g acrylic acid, 2.6 g N,N'-methylene bisacrylamide (0.8%-wt., relative to acrylic acid) were dissolved in 1000 ml water in a polymerization vessel and partially neutralized with 130 g sodium hydrogencarbonate. The catalyst components (0.3 g azobisamidine propane dihydrochloride, 0.6 g potassium peroxide disulfate, and 1.2 g sodium disulfite) dissolved in 120 ml water, were added at room temperature initiating the adiabatic polymerization. The resulting polymer gel was reduced in size, evenly sprayed with an aqueous solution of 2000 ppm (relative to the dry substance of the polymer gel) sodium peroxidisulfate, and mixed with component B.

Mixing of the polymer gel A with component B was carried out in a mixer produced with rotating stirring device. The device consists of a vertically or horizontally positioned metal cylinder (volume approx. 6000 ml), the mixing device of which is provided with guide blades to strip off thoroughly the walls of the mixing cylinder. After reaching a rotation speed of 300 rpm, a fluidized bed on the total length of the metal cylinder forms through the expelled individual particles of the mass when the rotary guide blades of the mixing device emerge. At this stage, the two components are evenly mixed and kneaded.

Subsequently, the resulting mass of polymer gel was dried within a recirculating air dryer at 120° C. and then ground. Starch being soluble in cold water was used as component B at different ratios. The absorption capacity of the end products was determined according to the DAT-method (Table 1).

TABLE 1

| Component A acrylic acid polymer %-wt. | Component B starch soluble in cold water %-wt. | | DAT-values retention (a) (ml/g) | DAT-values retention (b) (ml/g) |
|---|---|---|---|---|
| 100 | 0 | | 26.9 | 26.9 |
| 0 | 100 | smaller | 1.0 | — |
| Ex. 1: 91 | 9 | | 26.0 | 28.6 |
| Ex. 2: 83 | 17 | | 23.7 | 28.5 |
| Ex. 3: 67 | 33 | | 20.0 | 29.8 |

Note:
The DAT-value retention (a) relates to 1 g of the product composed of components A and B, retention (b) relates to 1 g of component

EXAMPLES 4 AND 5

Component A was produced according to the method as in Examples 1 to 3 and processed with alginate used as component B, The results are summarized in Table 2.

TABLE 2

| Component A acrylic acid polymer %-wt. | Component B alginate %-wt. | DAT-values retention (a) (ml/g) | DAT-values retention (b) (ml/g) |
|---|---|---|---|
| 100 | 0 | 26.9 | 26.9 |
| 0 | 100 | 12.1 | — |
| Ex. 4: 83 | 17 | 27.0 | 32.6 |
| Ex. 5: 67 | 33 | 26.5 | 39.6 |

Note:
The DAT-value retention (a) relates to 1 g of the product composed of components A and B, retention (b) relates to 1 g of component A in the product.

EXAMPLES 6 TO 8

A polymer gel having a cross-linking agent content of 0.6%-wt. (relative to polyacrylic acid) was produced according to the procedure of Examples 1 to 3; employed as component A, it was mixed with different amounts of corn starch in the described mixer and then processed according to the same manner as in Examples 1 to 3. In addition to the absorption capacity, the content of components A and B in the portions which are extractable with water was determined. The results are listed in the following table.

TABLE 3

| Component A acrylic acid polymer %-wt. | Component B corn starch %-wt. | | tea-bag-test-values retention (a) (ml/g) | tea-bag-test-values retention (b) (ml/g) |
|---|---|---|---|---|
| 100 | 0 | | 26.9 | 26.9 |
| 0 | 100 | smaller | 1.0 | — |
| Ex. 6: 91 | 9 | | 26.0 | 28.2 |
| Ex. 7: 83 | 17 | | 25.1 | 30.2 |
| Ex. 8: 71 | 29 | | 24.8 | 34.9 |

| | Soluble portions Component A % | | Component B % |
|---|---|---|---|
| | 3.5 | | — |
| Example 6: | 3.3 | smaller | 1.0 |
| Example 7: | 3.9 | | — |
| Example 8: | 4.5 | | 11.0 |

Note:
The tea bag test-value retention (a) relates to 1 g of the product composed of components A and B, retention (b) relates to 1 g of component A within the product.

EXAMPLES 9 AND 10

In a polymerization vessel, 370 g acrylic acid and 3.1 g N,N'-methylene bisacrylamide were dissolved in 410 ml water and neutralized with 460 g caustic-soda solution (45%). The catalyst components (0.26 azobisamidine propane dihydrochloride, 0.06 g benzil dimethyl ketal (Irgacure 651), and 0.26 g t-butyl hydroperoxide, dissolved in water) were added at room temperature and the adiabatic polymerization was started by UV-light. The achieved degree of reaction was 99.5%. The resulting polymer gel was reduced in size, dried to a water content of 8%-wt., ground and mixed with corn starch and moist viscose short fibers in a mixer according to Examples 1 to 3, and again dried a% 120° C. The results are listed in %he following table.

TABLE 4

| Component A acrylic acid polymer (%-wt.) | Component B corn starch (%-wt.) | Component B viscose fibers (%-wt.) | tea bag test-values maximum (ml/g) | | tea bag test-values retention (a) (ml/g) | tea bag test-values retention (b) (ml/g) |
|---|---|---|---|---|---|---|
| 100 | 0 | 0 | 39.8 | | 24.2 | 24.2 |
| 0 | 100 | 0 | 4.0 | smaller | 1.0 | — |
| 0 | 0 | 100 | 5.8 | | 1.0 | — |
| Ex. 9: 80 | 5 | 15 | 37.1 | | 23.8 | 29.7 |
| Ex. 10: 50 | 5 | 45 | 31.5 | | 15.4 | 30.8 |

Note:
The tea bag test values maximum and retention (a) relate to 1 g of the product composed of components A and B, retention (b) relates to 1 g of component A in the product

EXAMPLES 11 AND 12

According to the method of Examples 1 to 3, a polymer gel with a content of cross-linking agent of 0.4%-wt. (relative to polyacrylic acid) was produced and—used as component A—mixed and processed in a trough kneader with corn starch and different amounts of polyamide short fibers (1.0 mm, 6.7 dtex). The trough kneader (Werner & Pfleiderer, Stuttgart) consisted of a housing with a double-U-shaped cross-section, in which a pair of kneading shafts with two toothed, oppositely running sigma-blades moved. Processing within the kneader was terminated after 5 minutes; the resultant kneading mass was reduced in a meat grinder and dried at 120° C. The composition and the tea bag test-values are listed in the following table.

TABLE 5

| Component A | Component B | | tea bag test-values | | |
|---|---|---|---|---|---|
| acrylic acid | corn | polyamide | | retention | |
| polymer (%-wt.) | starch (%-wt.) | fibers (%-wt.) | maximum (ml/g) | (a) (ml/g) | (b) (ml/g) |
| 100 | 0 | 0 | 39.8 | | 30.2 | 30.2 |
| 0 | 100 | 0 | 4.0 | smaller | 1.0 | — |
| 0 | 0 | 100 | 4.5 | smaller | 1.0 | — |
| Ex. 11: 90 | 5 | 5 | 39.4 | | 27.5 | 30.6 |
| Ex. 12: 85 | 5 | 10 | 39.8 | | 27.4 | 32.2 |

Note:
The tea bag test values maximum and retention (a) relate to 1 g of the product composed of components A and B, retention (b) relates to 1 g of component A within the product.

EXAMPLES 13 AND 14

A polyacrylic acid polymer having a content of cross-linking agent of 0.8%-wt. was produced according to the process as in Example 9; it was then dried and ground. The finely ground size fraction of smaller than 150 µm was mixed with cellulose fibers (Arbocell 800, Rettenmayer, Holzkirchen) and processed in dry condition, or partially made into a paste with water, in a trough kneader as in Example 11 with the freshly made polymer gel manufactured according to Example 9. Processing in the kneader was terminated after 5 minutes; the resultant kneading mass was reduced in a meat grinder and dried at 150° C. The particle-size distribution of the end product with a fine-material-portion which was smaller than 150 µm of 22.6%-wt. may be compared to the particle-size distribution of a ground mass from a freshly produced polymer 9granulate of component A without any additives (20.1%-wt. fines smaller than 150 µm).

TABLE 6

| | Component A acrylic acid polymer (polymer gel) %-wt. | Component B acrylic acid polymer (size fraction smaller than 150 µm) %-wt. | cellulose fibers %-wt. | tea bag test-values retention | |
|---|---|---|---|---|---|
| | | | | (a) (ml/g) | (b) (ml/g) |
| | 100 | 0 | 0 | 26.9 | 26.9 |
| | 0 | 0 | 100 | 1.6 | — |
| Ex. 13: | 82 | 9 | 9 | 22.8 | 25.1 |
| Ex. 14: | 73 | 18 | 9 | 22.3 | 24.5 |

Note:
The tea bag test value retention (a) relates to 1 g of the product composed of components A and B, retention (b) relates to 1 g of component A in the product.

EXAMPLE 15

According to the procedure of Example 7, a polymer gel of polyacrylic acid with a cross-linking agent content of 0.3%-wt. was produced, dried and ground. The size fraction of smaller than 150 µm was made into a paste with water and processed as component B fin a trough kneader (Example 14). The resultant kneading mass was reduced in a meat grinder and mixed with freshly produced polymer gel at a Weight ratio of 1:4, dried at 150° C. and ground. The particle-size distribution of the end product with a moiety of fines being smaller than 150 µm of 19.5%-wt. may be compared to the particle-size distribution and the fine-grain proportion of a ground material from a freshly produced polymer granular material (20.1%-wt. fines). The end product has a retention of 31.0 ml/g.

According to the procedure as in Examples 1 to 3 a polymer gel having a content of cross-linking agent of 0.6%-wt. (relative to polyacrylic acid) was produced. Used as component A, it was mixed with different amounts of corn starch in a mixer as in Examples 1 to 3, and processed in the same manner as described in Examples 1 to 4. The powdery end product was swollen with water (200 g water per 1 g product), and the swollen gel was irradiated with the xenon test lamp to simulate artificial degradation conditions. After 30, 60, and 90 minutes, the degradability of the polymer gel was assessed according to a scale with grades 1 to 8, The results are summarized in the following table.

TABLE 9

| Component A Acrylic acid polymer | Component B Corn starch | Exposure time Minutes | | |
|---|---|---|---|---|
| %-wt. | %-wt. | 30 | 60 | 90 |
| 100 | 0 | 1 | 1 | 2 |
| 90 | 10 | 2 | 4 | 5 |
| 80 | 20 | 3 | 4 | 6 |
| 60 | 40 | 3 | 6 | 7 |

Grade 1: gel structure unchanged
Grade 2: gel structure slightly changed
Grade 3: gel structure still detectable, but slight flow
Grade 4: gel structure extremely flown
Grade 5: gel structure not detectable, a highly viscous liquid
Grade 6: low viscous liquid
Grade 7: liquid ressembling water
Grade 8: water completely evaporated

EXAMPLE 17

The polymerization was carried out in the trough kneader described in Example 14. During the polymerization the starch was incorporated in the polymer gel. In the kneader which was blown with nitrogen, 840 g acrylic acid, 5.88 g methylene bisacrylamide were dissolved in 1270 ml water first, and then partially neutralized with 725 g caustic-soda solution (45%). The catalyst components (3.3 g azobisamidine propane dihydrochloride, 3.0 g sodium peroxidisulfate, and 0.05 g ascorbic acid), dissolved in 150 ml water, were added at room temperature; the monomer solution was blown with nitrogen and the adiabatic polymerization started.

When a polymer conversion of approximately 60% was achieved, 84 g starch soluble in cold water (10%-wt., relative to acrylic acid) was stirred in portions into the forming soft polymer gel by means of the pair of kneading shafts and the polymerization was continued. Subsequently, the resultant mass of polymer gel was reduced in size, dried in a recirculating air dryer at 120° C. and then ground.

The absorption capacity of the end product (DAT-values) were 32 ml/g—maximum value and 21 ml/g—retention (a).

EXAMPLE 18

The polymerization was started in the trough kneader according to the procedure as described in Example 17, after a polymer conversion of approximately 30% was achieved, 168 g starch being soluble in cold water (20%-wt., relative to acrylic acid) was added to the soft polymer gel which was forming. The starch was incorporated in the polymer gel with the pair of kneading shafts. After the end of polymerization, the mass of polymer gel was reduced in size and dried as in Example 17.

The absorption capacity of the final product were 28 ml/g (DAT-maximum) and 20 ml/g—retention (a).

It is understood that the specification and examples are illustrative but not limitative of the present invention and that other embodiments within the spirit and scope of the invention will suggest themselves to those skilled in the art.

I claim:

1. A process for the production of a water absorptive material comprising
    1. polymerizing a monomer mixture comprising by weight
        a). 40–100% monomeric units selected from the group consisting of polymerizable acids, and salts, esters and amides of such acids,
        b). 0.01–2.0% of a cross-linking monomer having at least two functional groups, and
        c). 0–40% of a water-insoluble monomer,
    said monomers, upon polymerization, forming a water-swellable, synthetic polymer or copolymer, to a momomer conversion of at least 30% to form a polymer gel (component A),
    2. blending with said polymer gel a polysaccharide which is a pourable powder at normal temperature and is only partially soluble or insoluble in water (component B), said polysaccharide being blended with said polymer gel in dry or partially swollen form during the polymerization process of component A after said monomer conversion of at least 30%.
    3. drying the blend of the polymer gel and the polysaccharide to form a water-swellable polymer or copolymer based composition which retains high water absorptive capacity even though the polysaccharide with a low water absorptive capacity is blended therewith, the amount of water extractables from the product of component A and component B being less than the water extractables from the physical blend of component A and component B.

2. The process according to claim 1, wherein component B is added to component A only during the end phase of the production process of component A after a monomer conversion of more than 80% is attained.

3. The process according to claim 1, wherein component B is used in dried form as a powder.

4. The process according to claim 1, wherein component B is used in slightly swollen form.

5. The process according to claim 1, wherein a bond between component A and B is achieved by adding at least one radical-forming catalyst to component A or B.

6. The process according to claim 1, wherein, in addition to component B, a natural or a synthetic fiber is added.

7. The process according to claim 6, wherein said natural fiber is a fiber selected from the group consisting of wool, silk, cotton or cellulose and said synthetic fiber is a fiber selected from the group consisting of polyester, polyolefin, polyamide, polyvinyl alcohol, polyurethane, polyurea, or polyacrylonitrile.

8. The process according to claim 1, wherein a neutral filler alone or in admixture with component B, or the ground component A itself, in the form of a powder or partially swollen, is incorporated into component A.

9. The process according to claim 1, wherein at least one of peat, sand, clay, garden mold, ground shells of nuts or pomaceous fruit, Wood flour and chitin-containing flour is used as neutral filling agent.

10. The process according to claim 1, wherein the absorbing material consists essentially of A and B, component B consists essentially of a polysaccharide and component A is a copolymer consisting essentially of
    a) 40–100%-wt. of a water-soluble monomer selected from the group consisting of polymerizable acids, the salts thereof, the hydroxy-group-, amino-group-or ammonium-group-containing esters or amides of such acids, and acrylamide.
    b) 0.01–2.0%-wt. of a crosslinking monomer having at least two functional groups, and
    c) 0–40%-wt. of a water-insoluble monomer.

11. The process according to claim 1, wherein component A is a cross-linked polymer or copolymer comprising monomeric units of a polymerizable acid selected from the group consisting of acrylic acid, methacrylic acid, maleic acid, fumaric acid, itaconic acid, vinyl sulfonic acid and 2-acrylamido-2-methylpropane sulfonic acid.

12. The process according to claim 11, wherein component B is added to component A only during the end phase of the production process of component A after a monomer conversion of more than 80% is attained, a bond between component A and B is achieved by adding at least one radical-forming catalyst to component A or B, in addition to component B there is added to A a (a) natural fiber selected from the group consisting of wool, silk, cotton and cellulose or a fiber selected from the group consisting of polyester, polyolefin, polyamide, polyvinyl alcohol, polyurethane, polyurea and polyacrylonitrile, and (b) at least one of peat, sand, clay, garden mold, ground shells of nuts or pomaceous fruit, wood flour and chitin-containing flour as neutral filling agent, the product comprising 20 to 98%-wt. of component A and 2 to 80%-wt. of component B and the content of water-extractables being less than 30%-wt.

13. In the absorption and/or retention of water and/or an aqueous solution by contact with an absorbent and the subsequent controlled release of water and/or the aqueous solution, the improvement which comprises employing as said absorbent the absorbing material produced according to claim 12.

* * * * *